United States Patent
Hsieh (10) Patent No.: US 12,420,541 B2
(45) Date of Patent: Sep. 23, 2025

(54) MOLD AND GAS SENSOR SEALING METHOD USING MOLD

(71) Applicant: Wen-Lo Hsieh, Kaohsiung (TW)

(72) Inventor: Wen-Lo Hsieh, Kaohsiung (TW)

( * ) Notice: Subject to any disclaimer, the term of this patent is extended or adjusted under 35 U.S.C. 154(b) by 172 days.

(21) Appl. No.: 18/329,547

(22) Filed: Jun. 5, 2023

(65) Prior Publication Data

US 2024/0343033 A1 Oct. 17, 2024

(30) Foreign Application Priority Data

Apr. 14, 2023 (TW) ................... 112113984

(51) Int. Cl.
*B32B 38/18* (2006.01)
*B32B 37/18* (2006.01)
*G01D 11/24* (2006.01)
*G01N 33/00* (2006.01)

(52) U.S. Cl.
CPC .......... *B32B 38/1833* (2013.01); *B32B 37/18* (2013.01); *B32B 2327/18* (2013.01); *G01D 11/24* (2013.01); *G01N 33/0009* (2013.01)

(58) Field of Classification Search
CPC ............... G01N 33/0009; G01D 11/24; B32B 2327/18; B32B 38/1833
See application file for complete search history.

(56) References Cited

U.S. PATENT DOCUMENTS

| 2007/0209433 A1* | 9/2007 | Gehman | ............... G01F 1/6845 73/204.26 |
| 2019/0186960 A1* | 6/2019 | Jo | ...................... G01N 33/0009 |

FOREIGN PATENT DOCUMENTS

WO  WO-2022051743 A1 *  3/2022  ......... G01N 33/0031

* cited by examiner

*Primary Examiner* — Vishal I Patel
(74) *Attorney, Agent, or Firm* — Leong C. Lei (57) ABSTRACT

Disclosed is a gas sensor sealing method, including: providing a substrate, where a soldered dot is formed on an upper surface of the substrate; providing a sensing chip, where the sensing chip is arranged on the upper surface of the substrate, and electrically connected to the soldered dot; providing a cover body in which a protective film is embedded, to bond a top surface of the protective film with a lower surface of the cover body, where the cover body includes at least one through hole arranged opposite to the protective film; and pressing and sealing the substrate and the cover body by using a lamination fixture, to combine the cover body on the upper surface of the substrate and form a chamber together, to wrap the sensing chip in the chamber.

6 Claims, 9 Drawing Sheets

MOLD AND GAS SENSOR SEALING METHOD USING MOLD

BACKGROUND

Technical Field

The present invention relates to a mold, and in particular, to a mold configured to manufacture a cover body of a gas sensor for effectively preventing a protective film from falling off, and a sealing method in which the cover body manufactured by the mold is used to manufacture the gas sensor.

Related Art

Figure 1:
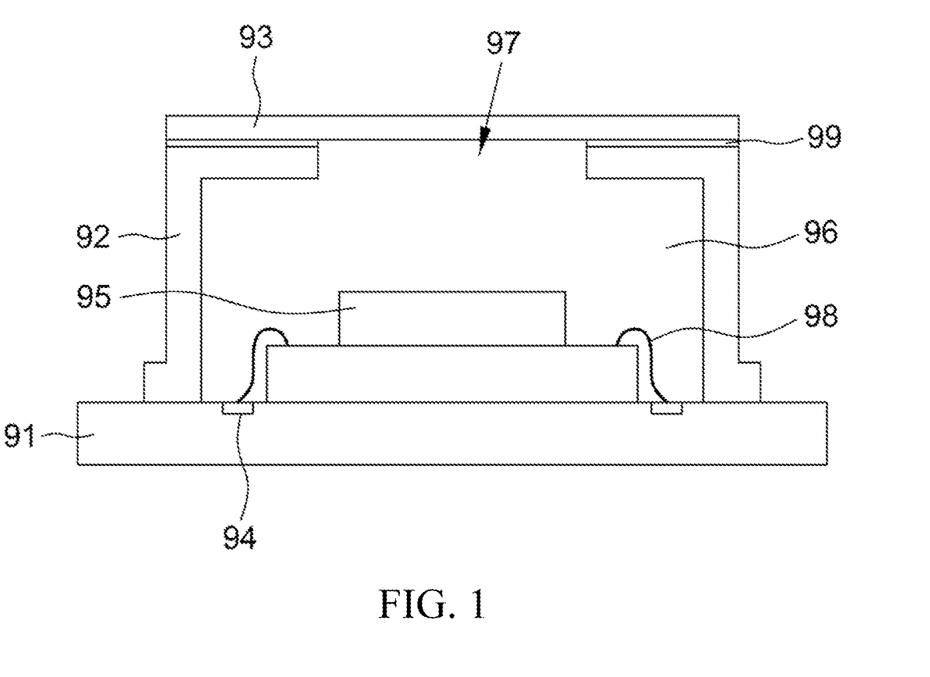
FIG. 1 is a sectional view of a conventional gas sensor sealing body.

FIG. 1 is a sectional view of a conventional gas sensor sealing body. The conventional gas sensor sealing body includes a substrate 91, a cover body 92, a protective film 93, a plurality of soldered dots 94, and a plurality of sensing chip 95. The cover body 96 is arranged above the substrate 91, and forms a chamber 96 together with the substrate 91. The cover body 92 includes a through hole 97 in communication with the chamber 96. The protective film 93 is arranged above the cover body 92, and can selectively allow outside gas to enter the chamber 96 through the through hole 97. The plurality of soldered dots 94 is arranged in the substrate 91 and located in the chamber 96. The plurality of sensing chips 95 is stacked on the substrate 91, and is electrically connected to the plurality of soldered dots 94 through wires 98. An adhesive layer 99 is included between the protective film 93 and the cover body 92, and the adhesive layer 99 is an adhesive such as a glue.

However, the adhesive layer 99 gradually loses viscosity as time changes, causing the protective film 93 to eventually fall off the cover body 92, so that all types of gas originally disallowed enter the chamber 96, further affecting the accuracy of the plurality of sensing chips 95, leading to a problem of poor sensing accuracy.

In view of this, it is necessary to provide a mold and a gas sensor sealing method using the mold, to resolve the foregoing problem.

SUMMARY

An objective of the present invention is to provide a mold that can manufacture a cover body of a gas sensor for effectively preventing a protective film from falling off.

Another objective of the present invention is to provide a gas sensor sealing method in which the cover body manufactured by the mold can be used to manufacture the gas sensor.

To achieve the objectives, the present invention provides a gas sensor sealing method, including: providing a substrate, where a soldered dot is formed on an upper surface of the substrate; providing a sensing chip, where the sensing chip is arranged on the upper surface of the substrate, and electrically connected to the soldered dot; providing a cover body in which a protective film is embedded, to bond a top surface of the protective film with a lower surface of the cover body, where the cover body includes at least one through hole arranged opposite to the protective film; and pressing and sealing the substrate and the cover body by using a lamination fixture, to combine the cover body on the upper surface of the substrate and form a chamber together, to wrap the sensing chip in the chamber.

In some embodiments, a PTFE film is selected as the protective film.

In some embodiments, the cover body forms a plurality of positioning posts, cross section areas of the positioning posts in a first direction are the same, the protective film generates a plurality of blind holes corresponding to the plurality of positioning posts, and the positioning posts are combined in the corresponding blind holes when the protective film is embedded in the cover body.

In some embodiments, the cover body forms a plurality of positioning posts, cross section areas of the positioning posts in a first direction gradually increase, the protective film generates a plurality of blind holes corresponding to the plurality of positioning posts, and the positioning posts are combined in the corresponding blind holes when the protective film is embedded in the cover body.

In some embodiments, at least one absorption layer is embedded in the cover body, and the at least one absorption layer is located between at least one through hole and the protective film.

In some embodiments, a support framework module is embedded in the cover body, a plurality of corners of the support framework module is respectively recessed towards a central arc to form a curved section for each corner, and the curved section and the protective film overlap each other in a first direction to fix the protective film.

The present invention further provides a mold, configured to manufacture a cover body in the foregoing gas sensor sealing method, and the mold includes: an upper mold, including a first cavity, and at least one first core configured to form the at least one through hole, where the first cavity includes a first inner diameter width, and the at least one first core extends along the first direction, is arranged in the first cavity, and includes a first molded surface; and a lower mold, opening and closing relative to the upper mold along the first direction, where the lower mold includes a second cavity and a second core, the second cavity includes a second inner diameter width equal to the first inner diameter width, the second core extends along an opposite direction of the first direction, is arranged in the second cavity, and includes a second molded surface, the second core is configured to carry the protective film, and in the first direction, a cross section area of the protective film is greater than a cross section area of the second core, and a width of the protective film is less than the second inner diameter width, where a molded cavity in communication with an injection port is formed by the first cavity and the second cavity together when the lower mold closes relative to the upper mold, the injection port is for a raw material of the cover body to flow into the molded cavity and is arranged in the upper mold or the lower mold, the at least one first core is arranged opposite to the second core, and a gap is formed in the first direction by the first molded surface and the second molded surface, so that the lower mold opens relative to the upper mold after the raw material cools down, and the cover body is manufactured.

In some embodiments, a plurality of first cores is provided and arranged at intervals.

In some embodiments, a thickness of the gap is less than a thickness of the protective film.

In some embodiments, the thickness of the gap is in a range of 20% to 50% of the thickness of the protective film.

In some embodiments, the protective film includes a plurality of blind holes extending in the first direction, and the at least one first core does not overlap the plurality of blind holes in the first direction, to manufacture the cover body.

In some embodiments, the second core is configured to carry the protective film and isolate at least one absorption layer of specific gas, the absorption layer is located between the protective film and the first core, and in the first direction, a cross section area of the first core is less than a cross section area of the absorption layer, the cross section area of the absorption layer is less than a cross section area of the second core, and the thickness of the gap is equal to a total thickness of the protective film and the absorption layer, to manufacture the corresponding cover body.

The mold and the gas sensor sealing method using the mold according to the present invention include the following features: The protective film can be embedded in the cover body when the cover body is molded, to bond the top surface of the protective film with the lower surface of the cover body, to prevent the protective film from falling off and increase the combined stability of the protective film and the cover body. Moreover, compared with a conventional gas sensor of the same overall axial height, the chamber of the gas sensor manufactured by the present invention has a larger space because the protective film is arranged inside the cover body, to contain more layers of sensing chips.

DETAILED DESCRIPTION

Embodiments of the present invention are described in detail below with reference to the accompanying drawings. The accompanying drawings are mainly simplified schematic diagrams, to exemplarily illustrate a basic structure of the present invention. Therefore, the accompanying drawings only mark elements related to the invention, and the shown elements are not drawn according to the quantity, shape, and dimensional proportion during implementation. In actual implementation, the dimension is a selective design, and the layout of the elements may be more complicated.

The following embodiments are described with reference to the accompanying drawings, which are used to exemplify specific embodiments for implementation of the present invention. Terms about directions mentioned in the present invention, such as "upper", "lower", "front", and "back", merely refer to directions in the accompanying drawings. Therefore, the used terms about directions are used to describe and understand this application, and are not intended to limit this application. In addition, throughout this specification, unless otherwise explicitly described to have an opposite meaning, the word "include" is understood as including the element, but not excluding any other element.

Figure 2:
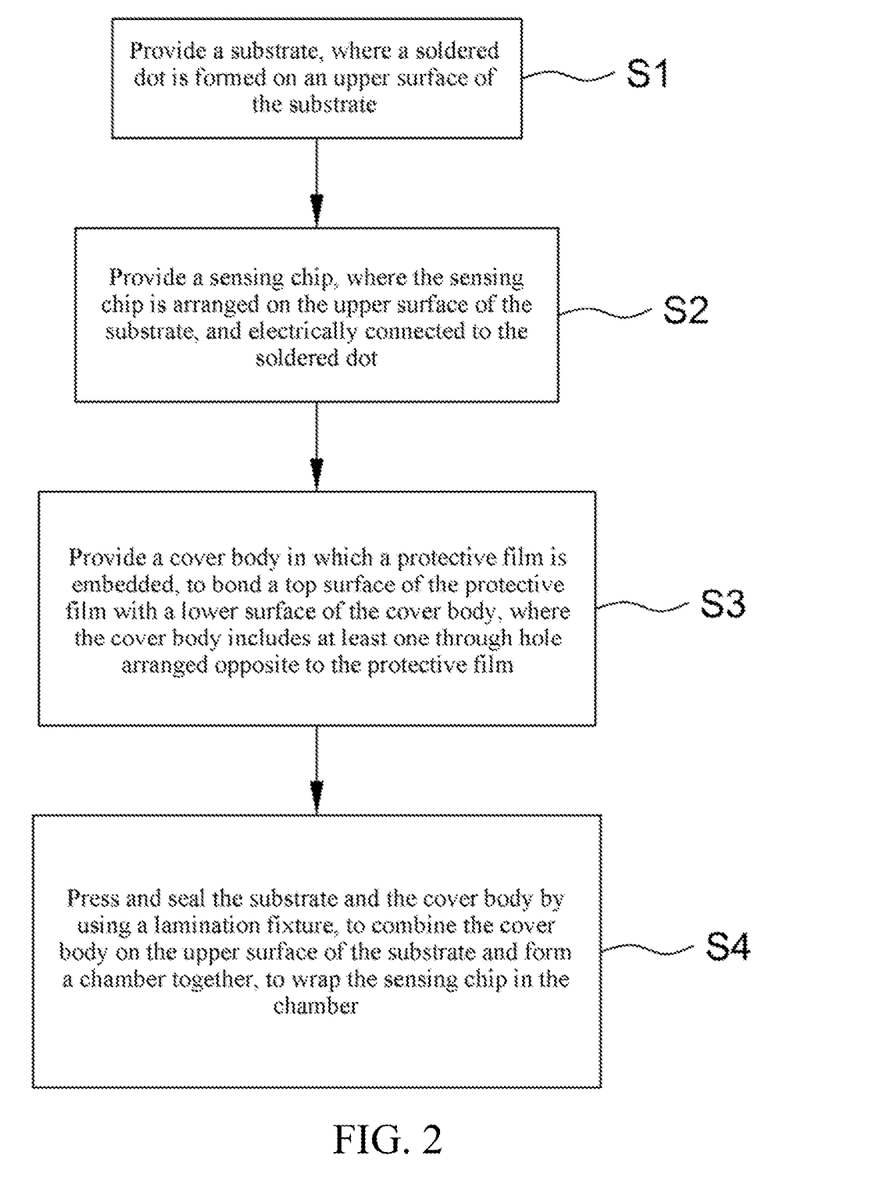
FIG. 2 is a method flowchart of a first embodiment of a gas sensor sealing method according to the present invention.
Figure 3:
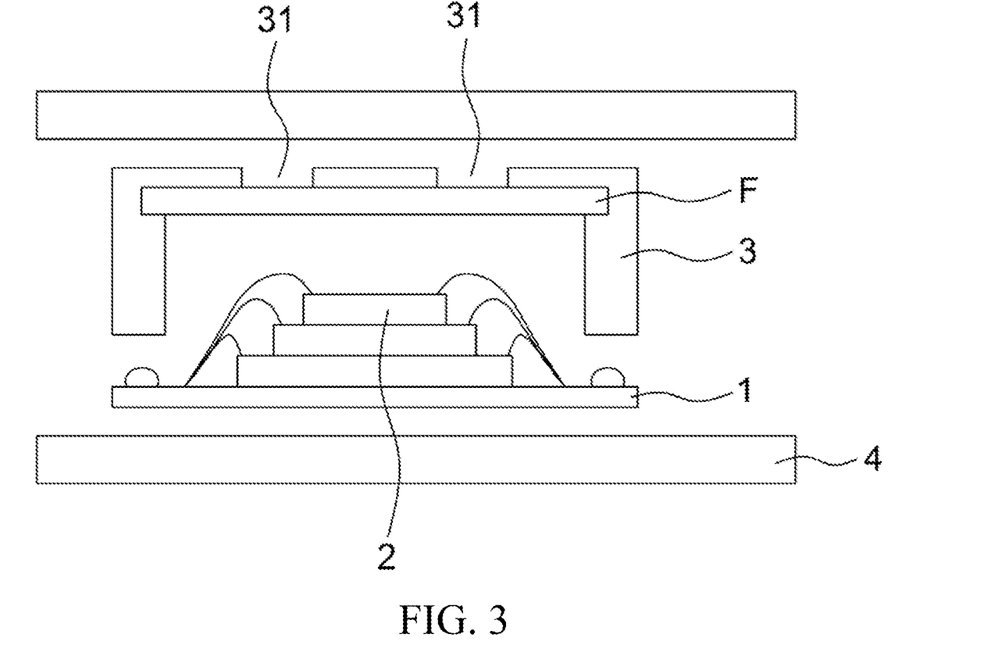
FIG. 3 is a sectional view of a gas sensor manufactured in a first embodiment of the gas sensor sealing method according to the present invention.
Figure 4:
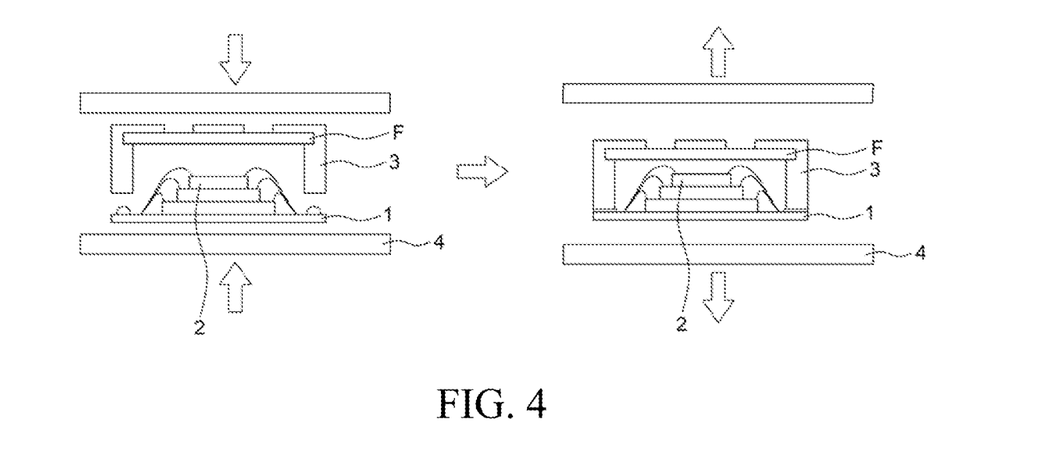
FIG. 4 is an action situation diagram of FIG. 3.

FIG. 2 to FIG. 4 show a first embodiment of a gas sensor sealing method according to the present invention. The method includes the following steps:

First step S1: Provide a substrate 1, where a soldered dot is formed on an upper surface of the substrate 1. In this embodiment, the substrate 1 is a printed circuit board or a flexible circuit board, and the soldered dot is electrically connected to an electronic component on the upper surface of the substrate 1.

Second step S2: Provide a sensing chip 2, where the sensing chip 2 is arranged on the upper surface of the substrate 1, and electrically connected to the soldered dot. Specifically, the sensing chip 2 is electrically connected to the soldered dot through a wire, and the wire may be a metal wire with high conductivity such as a gold, silver, or copper wire.

In the present invention, the sensing chip 2 is configured to sense gas, and may be selectively used according to a gas type to be sensed. For example, one of a hydrogen sulfide sensing chip, a carbon monoxide sensing chip, a carbon dioxide sensing chip, a flammable gas sensing chip, a volatile organic gas sensing chip, a nitrogen dioxide sensing chip, an ammonia sensing chip, or a chlorine dioxide sensing chip may be selected as the sensing chip, to respectively sense hydrogen sulfide, carbon monoxide, carbon dioxide, flammable gas, volatile organic gas, nitrogen dioxide, ammonia, and chlorine dioxide.

In another embodiment, a plurality of sensing chips 2 is further provided and stacked on one another, and adheres on the upper surface of the substrate 1 through epoxy or another adhesive polymer molding material.

Third step S3: Provide a cover body 3 in which a protective film F is embedded, to bond a top surface of the protective film F with a lower surface of the cover body 3, where the cover body 3 includes at least one through hole 31 arranged opposite to the protective film F. The protective film F may selectively allow a specific gas to pass through. In this embodiment, a PTFE film is selected as the protective film F.

Fourth step S4: Press and seal the substrate 1 and the cover body 3 by using a lamination fixture 4, to combine the cover body 3 on the upper surface of the substrate 1 and form a chamber together, to wrap the sensing chip 2 in the chamber. In this embodiment, a polymer adhesive is used to adhere the cover body 3 on the upper surface of the substrate 1. In this way, the manufacturing of the gas sensor according to the present invention can be completed.

Figure 5:
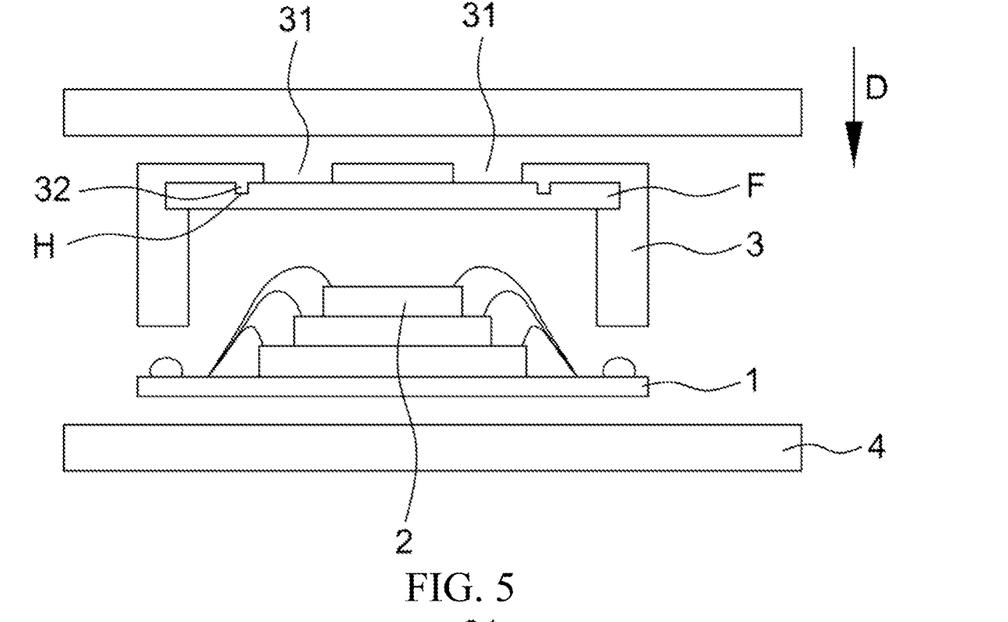
FIG. 5 is a sectional view of a gas sensor manufactured in a second embodiment of the gas sensor sealing method according to the present invention.

FIG. 5 shows a second embodiment of the gas sensor sealing method according to the present invention. A difference from the first embodiment is: A plurality of positioning posts may be further formed on the cover body 3 provided in the third step S3, and cross section areas of the positioning posts 32 in a first direction D are the same. The protective film F embedded in the cover body 3 may generate a plurality of blind holes H corresponding to the plurality of positioning posts 32 in a mechanical, optical or chemical manner, so that the positioning posts 32 may be combined in the corresponding blind holes H when the protective film F is embedded in the cover body 3, to form an anchoring function, and laterally combine the protective film with the cover body. In this embodiment, the positioning posts 32 is in a cylindrical shape and in the first direction D. The plurality of blind holes H does not overlap the at least one through hole 31.

It should be noted that, in this embodiment, a diameter of the blind hole H adjacent to the through hole 31 may be further designed to be 80% of a thickness of the protective film F. Furthermore, a thickness of a gap between two adjacent blind holes H may be designed as 60% of the thickness of the protective film F.

Figure 6:
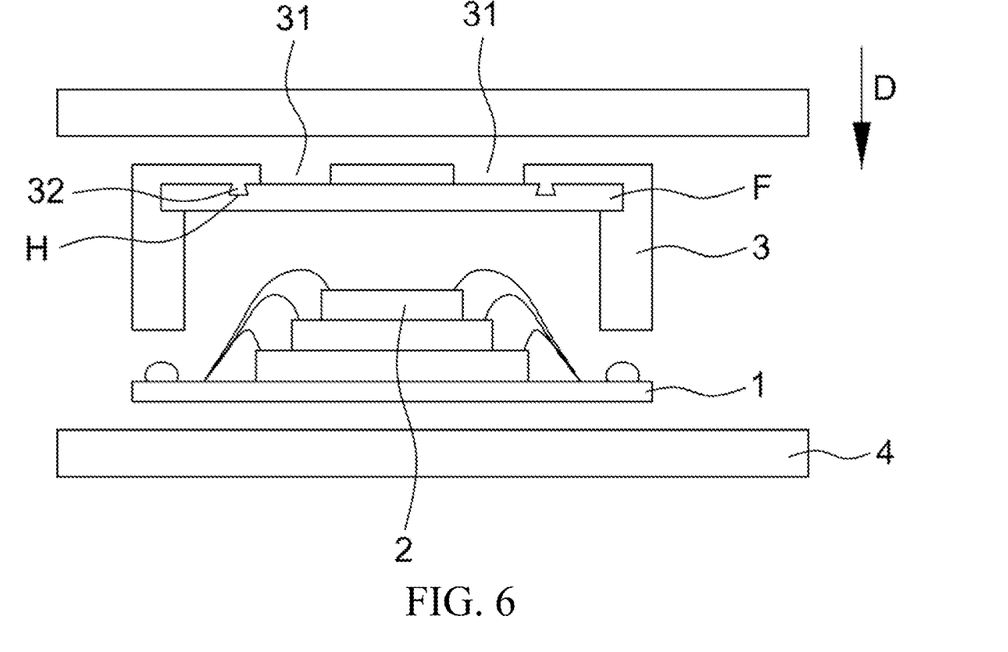
FIG. 6 is a sectional view of a gas sensor manufactured in a third embodiment of the gas sensor sealing method according to the present invention.

FIG. 6 shows a third embodiment of the gas sensor sealing method according to the present invention. A difference from the second embodiment is: Cross section areas of the positioning posts 32 in a first direction D gradually increase. In this embodiment, the positioning post 32 is in a shape of a truncated cone, and can increase the combined strength of the protective film laterally combined with the cover body. Preferably, an angle formed between a bottom surface of the positioning post 32 away from the lower surface of the cover body 3 and a side surface of the positioning post 32 is in a range of 45 degrees and 80 degrees.

Figure 7:
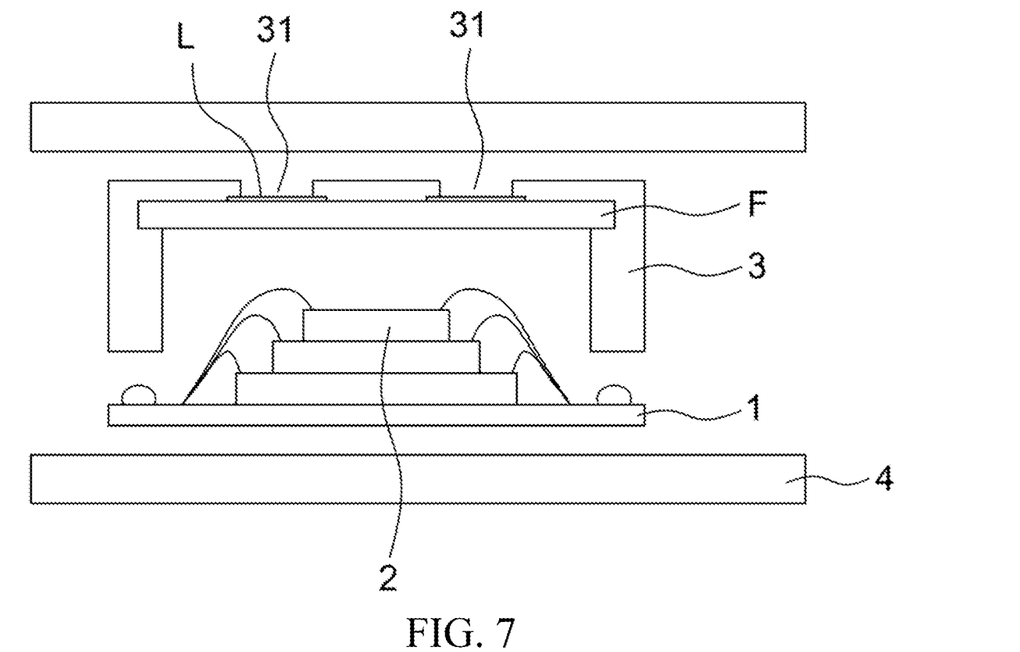
FIG. 7 is a sectional view of a gas sensor manufactured in a fourth embodiment of the gas sensor sealing method according to the present invention.

FIG. 7 shows a fourth embodiment of the gas sensor sealing method according to the present invention. A difference from the first embodiment is: At least one absorption layer L is further embedded in the cover body 3 provided in the third step S3, and the at least one absorption layer L is located between the at least one through hole 31 and the protective film F, to isolate gas not to be sensed by the sensing chip 2 from the chamber, thereby stabilizing the accuracy of the sensing chip and improving a yield rate. In this embodiment, active carbon, porous ceramics, or metal oxides may be selected as the absorption layer L.

Figure 8:
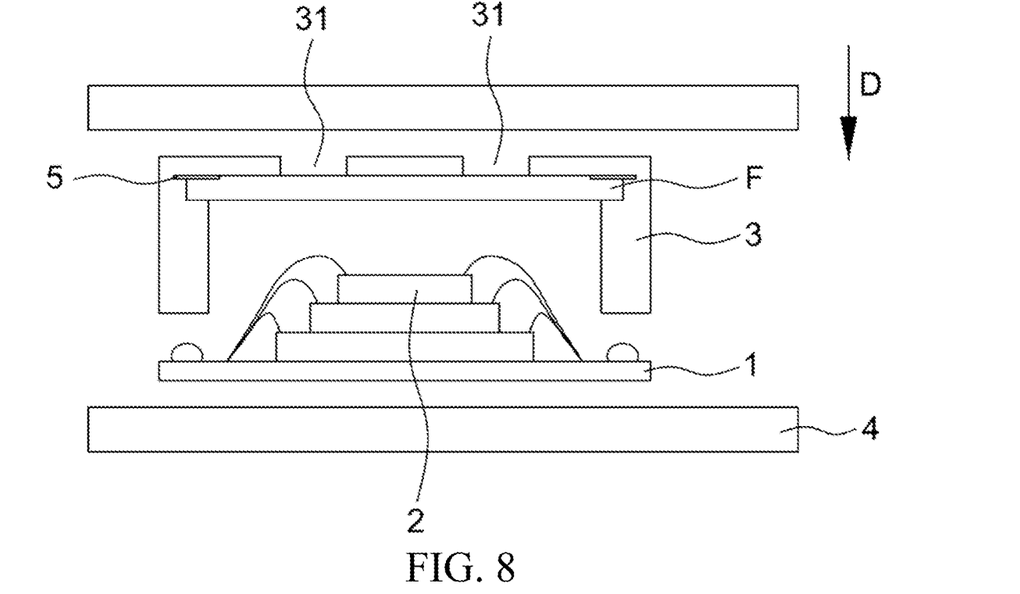
FIG. 8 is a sectional view of a gas sensor manufactured in a fifth embodiment of the gas sensor sealing method according to the present invention.
Figure 9:
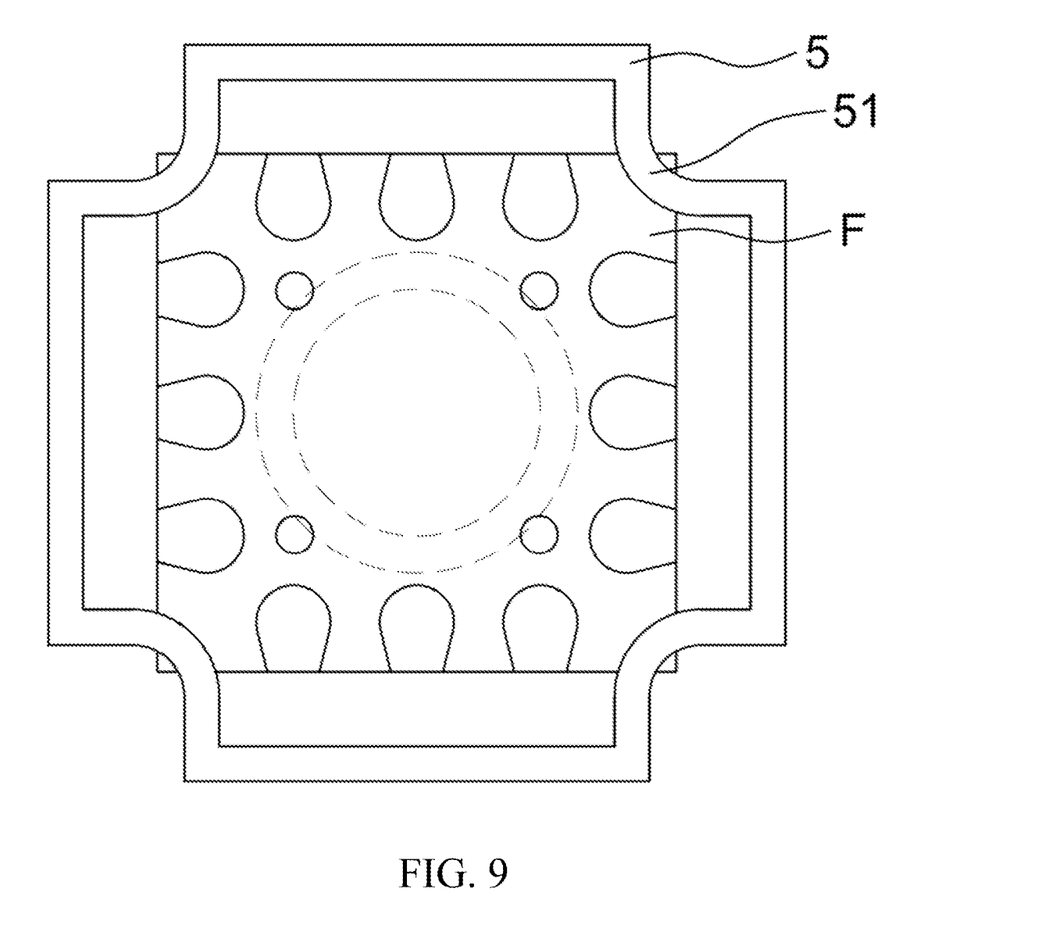
FIG. 9 is a top view of a support framework module in FIG. 8 combining and fixing a protective film.

FIG. 8 to FIG. 9 show a fifth embodiment of the gas sensor sealing method according to the present invention. A difference from the first embodiment is: The protective film F embedded in the cover body 3 may be combined and fixed by a support framework module 5 in the third step S3. Specifically, a plurality of corners of the support framework module 5 is respectively recessed towards a central arc to form a curved section 51 for each corner. The curved section 51 and the protective film F overlap each other in the first direction D to fix the protective film F. In this way, the shape of the severed protective film F is less likely to be uneven when the protective film F is fixed to the support framework module 5, to improve the efficiency of the gas sensor sealing structure.

Figure 10:
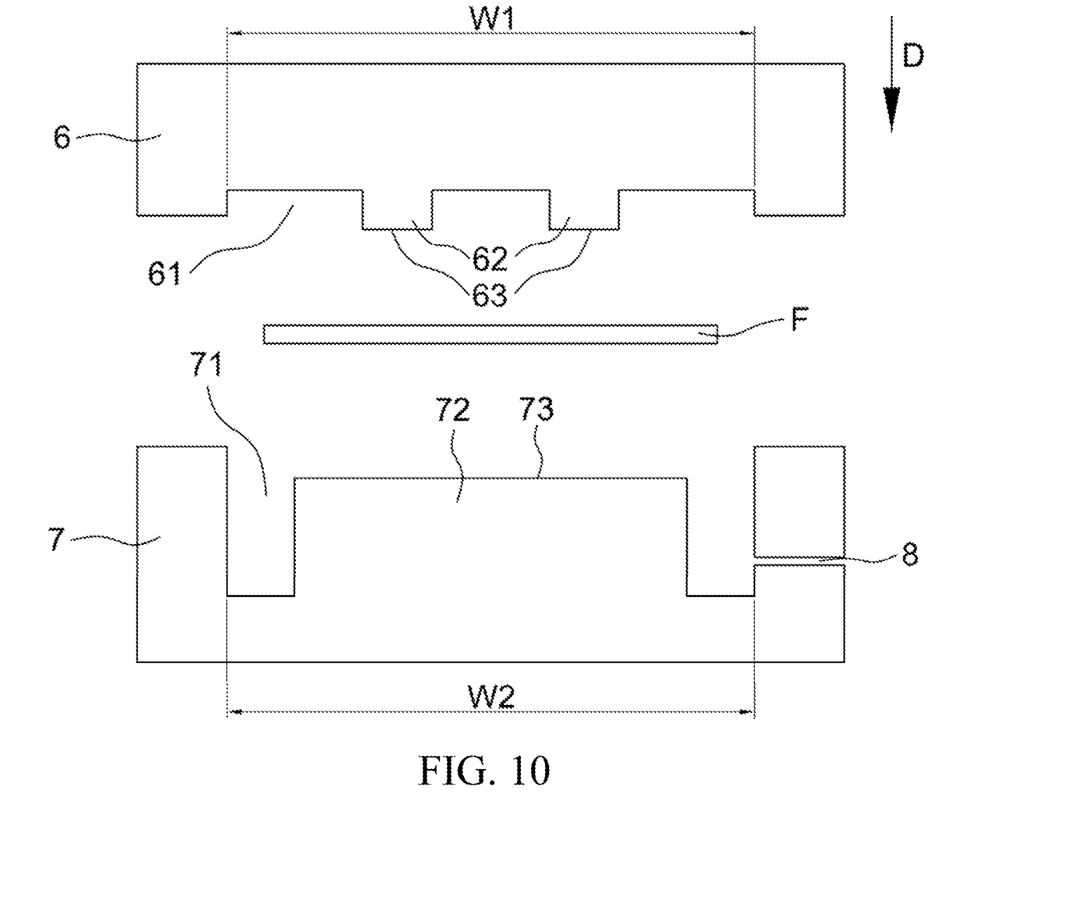
FIG. 10 is a sectional view of a mold in an open state in a first embodiment of the present invention.
Figure 11:
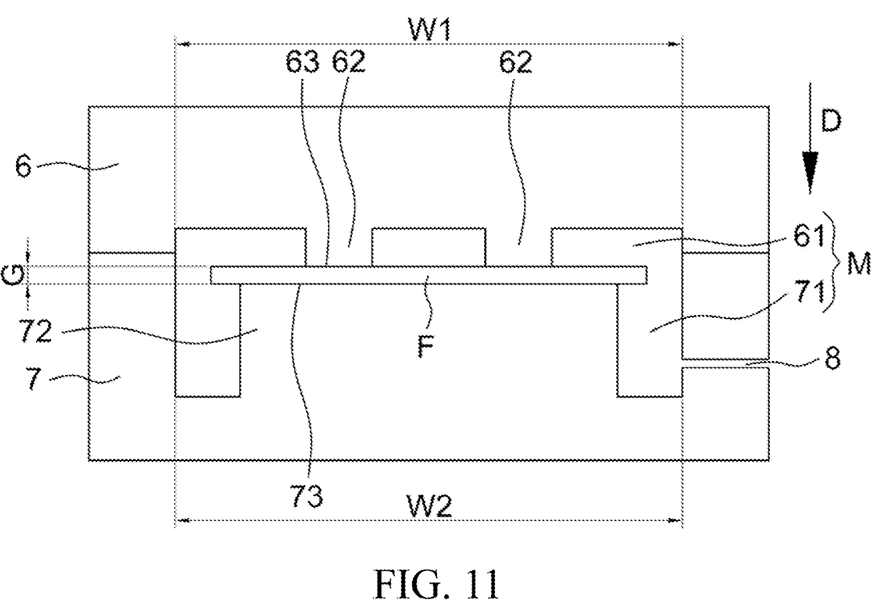
FIG. 11 is a sectional view of a mold in a closed state in the first embodiment of the present invention.

FIG. 10 to FIG. 11 show a first embodiment of the mold according to the present invention. The mold is configured to manufacture the cover body in the gas sensor sealing method described above, and the mold includes: an upper mold 6 and a lower mold 7. The lower mold 7 may open and close relative to the upper mold 6 along the first direction D.

The upper mold 6 includes a first cavity 61, and at least one first core 62 configured to form the at least one through hole 31, where the first cavity 61 includes a first inner diameter width W1, and a first inner diameter length (not shown in the figures). The at least one first core 62 extends along the first direction D, is arranged in the first cavity 61, and includes a first molded surface 63. In this embodiment, a plurality of first cores 62 are provided and arranged at intervals, and the first molded surface 63 may be in a rectangular shape or an oval shape.

The lower mold 7 is arranged parallel to the upper mold 6, and includes a second cavity 71 and a second core 72, where the second cavity 71 includes a second inner diameter width W2 equal to the first inner diameter width W1, and a second inner diameter length (not shown in the figures) equal to the first inner diameter length. The second core 72 extends along an opposite direction of the first direction D, is arranged in the second cavity 71, and includes a second molded surface 73.

The second core 72 is configured to carry the protective film F, and in the first direction D, a cross section area of the protective film F is greater than a cross section area of the second core 72, a width of the protective film is less than the second inner diameter width W2, and a length of the protective film F is less than the second inner diameter length. It should be noted that, the protective film F has no contact with an inner wall of the lower mold 7 when the protective film F is placed above the second core 72.

A molded cavity M in communication with an injection port 8 is formed by the first cavity 61 and the second cavity 71 together when the lower mold 7 closes relative to the upper mold 6. The injection port 8 is for a raw material of the cover body 3 to flow into the molded cavity M and is arranged in the upper mold 6 or the lower mold 7. In this embodiment, an example in which the injection port 8 is arranged in the lower mold 7 is used for description.

Referring to FIG. 3 together, the first core 62 is arranged opposite to the second core 72, and a gap G is formed in the first direction D by the first molded surface 63 and the second molded surface 73. In this embodiment, a thickness of the gap G is equal to the thickness of the protective film F. The lower mold 7 opens relative to the upper mold 6 after the raw material cools down, and the cover body 3 is manufactured. In this way, the protective film F can be embedded in the cover body 3 in a manufacturing process, and the top surface of the protective film F is bonded with the lower surface of the cover body C, to prevent the protective film from falling off the cover body.

Figure 12:
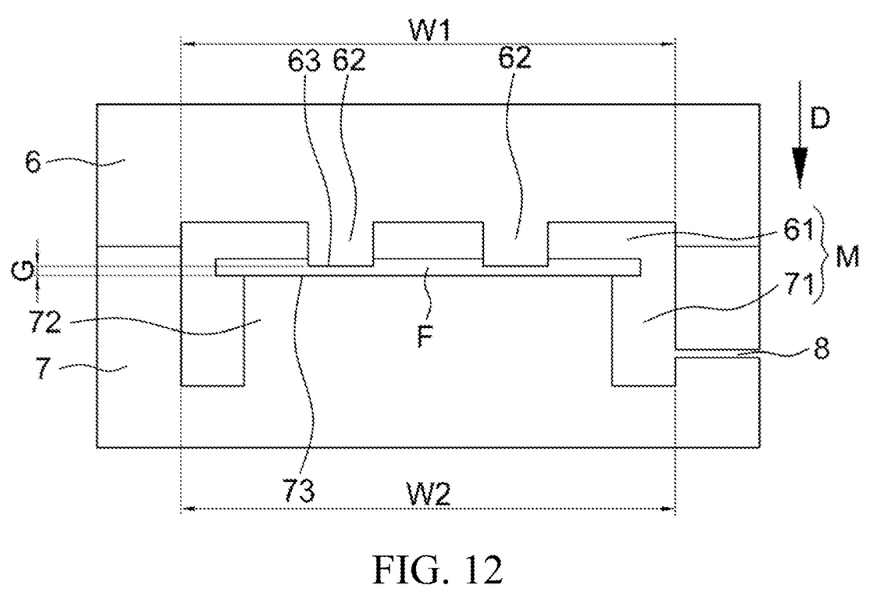
FIG. 12 is a sectional view of a mold in a closed state in a second embodiment of the present invention.

FIG. 12 shows a second embodiment of the mold according to the present invention. A difference from the first embodiment is: The thickness of the gap G is less than the thickness of the protective film F, and the thickness of the gap G is preferably in a range of 20% to 50% of the thickness of the protective film F. In this way, the protective film F is pressed tightly by the first core 62 when the lower mold 7 closes relative to the upper mold 6, to reduce the thickness of the protective film F to a range of 50% to 80% of the original thickness, to avoid failing to form the through hole as the raw material flows between the first core 62 and the protective film F.

Figure 13:
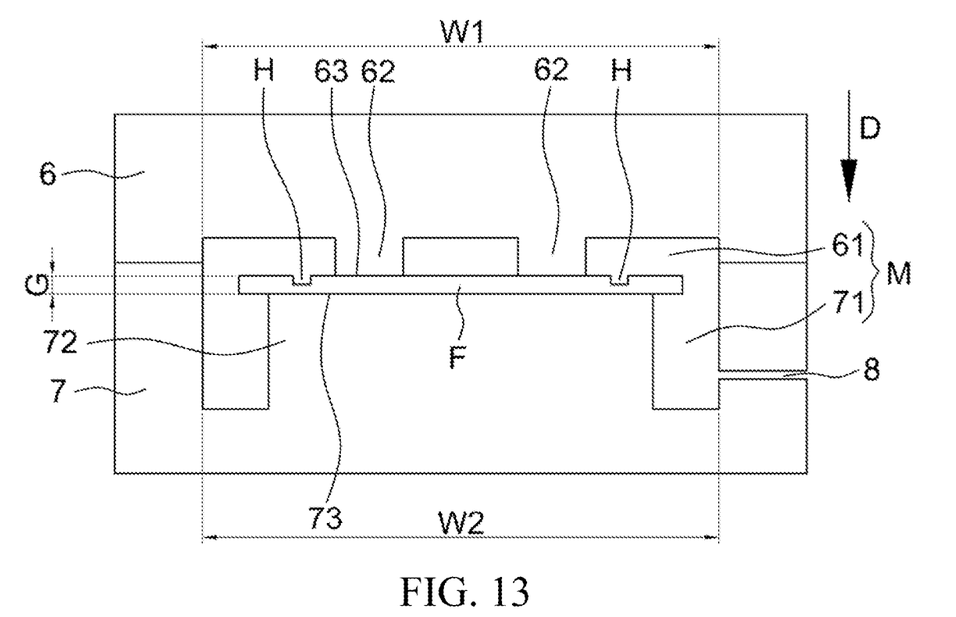
FIG. 13 is a sectional view of a mold in a closed state in a third embodiment of the present invention.

FIG. 5, FIG. 6, and FIG. 13 show a third embodiment of the mold according to the present invention. A difference from the first embodiment is: The protective film F includes a plurality of blind holes H extending in the first direction D, and the at least one first core 62 does not overlap the plurality of blind holes H in the first direction D. In this embodiment, the diameter of the blind hole H in the first direction D may be the equal or gradually increasing, to manufacture the corresponding cover body 3.

Figure 14:
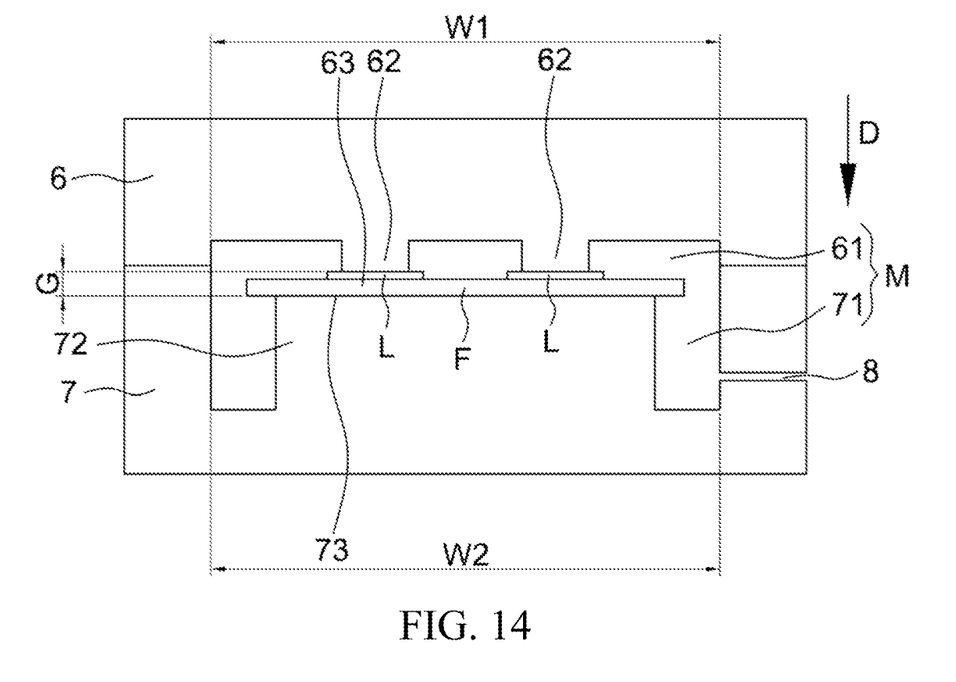
FIG. 14 is a sectional view of a mold in a closed state in a fourth embodiment of the present invention.

FIG. 7 and FIG. 14 show a fourth embodiment of the mold according to the present invention. A difference from the first embodiment is: The second core 72 is configured to carry the protective film F and at least one absorption layer L for isolating specific gas. The absorption layer L is located between the protective film F and the first core 62, and in the first direction D, a cross section area of the first core 62 is less than a cross section area of the absorption layer L, the cross section area of the absorption layer L is less than a cross section area of the second core 72, and the thickness of the gap G is equal to aggregate total thickness of the protective film F and the absorption layer L, to manufacture the corresponding cover body 3.

To sum up, according to the mold and the gas sensor sealing method using the mold according to the present invention, the protective film can be embedded in the cover body when the cover body is molded, to bond the top surface of the protective film with the lower surface of the cover body, to prevent the protective film from falling off and increase the combined stability of the protective film and the cover body. Moreover, compared with a conventional gas sensor of the same overall axial height, the chamber of the gas sensor manufactured by the present invention has a larger space because the protective film is arranged inside the cover body, to contain more layers of sensing chips.

The foregoing disclosed implementations merely exemplarily describe the principles, features, and effects of the present invention, but are not intended to limit the scope of implementations of the present invention, and any one skilled in the art can modify and change the foregoing implementations without departing from the spirit and scope of the present invention. Any equivalent change and modification according to the disclosed content of the present invention shall fall within the scope of the following claims.

What is claimed is:

1. A gas sensor sealing method, comprising steps of:
providing a substrate, wherein a soldered dot is formed on an upper surface of the substrate;
providing a sensing chip, wherein the sensing chip is arranged on the upper surface of the substrate, and electrically connected to the soldered dot;
providing a cover body in which a protective film is embedded, to bond a top surface of the protective film with a lower surface of the cover body, wherein the cover body comprises at least one through hole arranged opposite to the protective film; and
pressing and sealing the substrate and the cover body by using a lamination fixture, to combine the cover body on the upper surface of the substrate and form a chamber together, to wrap the sensing chip in the chamber.

2. The gas sensor sealing method according to claim 1, wherein a PTFE film is selected as the protective film.

3. The gas sensor sealing method according to claim 1, wherein the cover body forms a plurality of positioning posts, cross section areas of the positioning posts in a first direction are the same, the protective film generates a plurality of blind holes corresponding to the plurality of positioning posts, and the positioning posts are combined in the corresponding blind holes when the protective film is embedded in the cover body.

4. The gas sensor sealing method according to claim 1, wherein the cover body forms a plurality of positioning posts, cross section areas of the positioning posts in a first direction gradually increase, the protective film generates a plurality of blind holes corresponding to the plurality of positioning posts, and the positioning posts are combined in the corresponding blind holes when the protective film is embedded in the cover body.

5. The gas sensor sealing method according to claim 1, wherein at least one absorption layer is embedded in the cover body, and the at least one absorption layer is located between the at least one through hole and the protective film.

6. The gas sensor sealing method according to claim 1, wherein a support framework module is embedded in the cover body, a plurality of corners of the support framework module is respectively recessed towards a central arc to form a curved section for each corner, and the curved section and the protective film overlap each other in a first direction to fix the protective film.

* * * * *